(12) United States Patent
Pei et al.

(10) Patent No.: US 12,112,447 B2
(45) Date of Patent: Oct. 8, 2024

(54) METHOD FOR IDENTIFYING, LOCATING AND TRACKING CALIBRATING CONDUIT WITHIN 3D ULTRASOUND POINT CLOUD

(71) Applicant: JIANGSU TINGSN TECHNOLOGY CO., LTD, Nanjing (CN)

(72) Inventors: Ruifeng Pei, Nanjing (CN); Weijie Qin, Nanjing (CN)

(73) Assignee: JIANGSU TINGSN TECHNOLOGY CO., LTD, Nanjing (CN)

(*) Notice: Subject to any disclaimer, the term of this patent is extended or adjusted under 35 U.S.C. 154(b) by 0 days.

(21) Appl. No.: 18/266,831

(22) PCT Filed: Feb. 28, 2023

(86) PCT No.: PCT/CN2023/078617
§ 371 (c)(1),
(2) Date: Dec. 25, 2023

(87) PCT Pub. No.: WO2024/016670
PCT Pub. Date: Jan. 25, 2024

(65) Prior Publication Data
US 2024/0265657 A1    Aug. 8, 2024

(30) Foreign Application Priority Data

Jul. 20, 2022 (CN) .................. 202210854447.X

(51) Int. Cl.
*G06T 19/20* (2011.01)
*G06V 10/34* (2022.01)
(Continued)

(52) U.S. Cl.
CPC .............. *G06T 19/20* (2013.01); *G06V 10/34* (2022.01); *G06V 10/44* (2022.01); *G06V 10/764* (2022.01);
(Continued)

(58) Field of Classification Search
CPC . G06T 19/20; G06T 2200/24; G06T 2210/41; G06T 2219/2012; G06V 10/34; G06V 10/44; G06V 10/764
See application file for complete search history.

(56) References Cited

U.S. PATENT DOCUMENTS

| 10,169,680 B1 | 1/2019 | Sachdeva et al. |
| 2010/0073150 A1* | 3/2010 | Olson ............... A61B 34/74 340/407.1 |

(Continued)

FOREIGN PATENT DOCUMENTS

| CN | 101196988 A | 6/2008 |
| CN | 105741324 A | 7/2016 |

(Continued)

*Primary Examiner* — Sing-Wai Wu
(74) *Attorney, Agent, or Firm* — Bayramoglu Law Offices LLC

(57) ABSTRACT

A method for identifying, locating and tracking a calibrating conduit within a 3D ultrasound point cloud includes the following steps: firstly rapidly modeling the conduit through an ultrasound map, then framing an approximate range of the conduit after human-computer interaction in a display interface, and tracking the approximate range accurately. The method has advantages of modeling and locating the conduit based on pure ultrasound, faster and more accurate modeling, more accurate positioning of the conduit by framing, reducing inaccurate positioning caused by other factors, and human-machine interaction for positioning the conduit with ready access to ensure accuracy and reliability. Further, this conduit localization algorithm reduces overall process time and provides a clearer and more real-time image of the conduit in a target environment, eliminating need for an overly demanding target environment and fixed reference points introduced by the conduit, while being more accurate than relying solely on ultrasound modeling.

13 Claims, 1 Drawing Sheet

(51) Int. Cl.
*G06V 10/44* (2022.01)
*G06V 10/764* (2022.01)

(52) U.S. Cl.
CPC ...... *G06T 2200/24* (2013.01); *G06T 2210/41* (2013.01); *G06T 2219/2012* (2013.01)

(56) References Cited

U.S. PATENT DOCUMENTS

| | | | | |
|---|---|---|---|---|
| 2013/0102889 | A1* | 4/2013 | Southard | C08G 61/125 600/424 |
| 2015/0228406 | A1* | 8/2015 | Corl | A61B 8/445 29/606 |
| 2017/0262105 | A1* | 9/2017 | Li | G06F 3/0488 |
| 2020/0179060 | A1* | 6/2020 | Kopel | A61B 6/50 |
| 2020/0305970 | A1* | 10/2020 | Ben-Haim | A61B 5/6852 |
| 2022/0249065 | A1* | 8/2022 | Torii | A61B 8/4461 |

FOREIGN PATENT DOCUMENTS

| | | |
|---|---|---|
| CN | 110025378 A | 7/2019 |
| CN | 115082647 A | 9/2022 |

\* cited by examiner

METHOD FOR IDENTIFYING, LOCATING AND TRACKING CALIBRATING CONDUIT WITHIN 3D ULTRASOUND POINT CLOUD

CROSS-REFERENCES OF THE RELATED APPLICATIONS

This application is the national phase entry of International Application No. PCT/CN2023/078617, filed on Feb. 28, 2023, which is based upon and claims priority to Chinese Patent Application No. 202210854447.X, filed on Jul. 20, 2022, the entire contents of which are incorporated herein by reference.

TECHNICAL FIELD

The present invention relates to identification and localization of an ultrasonic conduit, and in particular, to a method for identifying, locating and tracking a calibrating conduit within a three-dimensional (3D) ultrasound point cloud.

BACKGROUND

Three-dimensional calibration and conduit navigation technology currently can establish a 3D model based on two-dimensional (2D) ultrasound image information and can directly observe an internal structure of a model. A conduit is a device for assisting in imaging and ablation. The conduit is introduced into a target environment using imaging equipment. A position location of a conduit highlight can be obtained from an ultrasound image. However, when working in a complex environment, this process requires precise operation by a user and relies on the experience and ability of the user. Therefore, the accuracy of conduit location information is extremely important. In the last two to three decades, some conduit positioning and navigation technology has made great progress. However, there are still many shortcomings in these positioning and navigation technology and a related system. For example, positioning technology based on a 3D magnetic field has the defects that the target environment and fixed reference points introduced by the conduit may be moved relatively, which affect the accuracy of positioning. Further improvement and development is needed in the identification and tracking of the conduit. It is the inevitable trend to study a more efficient and accurate tracking and positioning method for 3D positioning and navigation technology of the conduit.

A 3D electrophysiological calibration system in the prior art uses three types of positioning navigation technology, respectively: a magnetic field positioning method, a electrical impedance positioning method, and a magnetoelectric combination method. The magnetic field positioning method forms a positioning system based on a magnetic pole in the conduit and the position of the reference electrode attached to the surface of the environment introduced by the conduit. Regarding the electrical impedance method, the environmental surface needs to wrap a large number of electrode devices, and then record a unipolar conductance electrogram of each electrode in turn, record the unipolar conductance electrogram of all electrodes, perform Computed Tomography (CT) scan of the environment covered with an electrode device, and then integrate and construct a 3D model of electrical signals.

The use of a magnetoelectric point location has many disadvantages of affecting the accuracy of imaging, specifically: there is dependence on the user's experience and ability; relative movement of the target environment and the fixed reference point introduced by the conduit affects the accuracy of positioning; the magnetoelectric point location is expensive and costly; a positioning density is low, and the corresponding accuracy is reduced.

Technical Problems

The 3D electrophysiological calibration system in the prior art uses positioning navigation technology, which has many disadvantages of relying on user experience, inaccurate positioning, low positioning density, and being expensive and costly.

SUMMARY

To solve the above problems, the present invention provides a method for identifying, localizing and tracking a calibrating conduit within a 3D ultrasound point cloud, comprising the following steps: Step S01: modeling an interior of a target environment; Step S02: performing human-computer interaction to locate a conduit in a user operation interface, and placing the conduit into a scannable range of an ultrasound probe; Step S03: after starting tracking and placing the conduit into the scannable range of the probe, performing, by the user, human-computer interaction operation on a display interface to frame an area where the conduit is located, and giving the content in the frame a color to distinguish therefrom; making, by the user, a determination whether the conduit position is accurate, and if the framing is not correct, the user frames again until the conduit position is accurately identified; Step S04: after the conduit position is accurately identified, obtaining a range for positioning the conduit, and identifying and tracking the conduit; Step S05: identifying and obtaining the point cloud of the target conduit, and taking the obtained point cloud as an input to obtain a field point cloud generated from a 2D ultrasound image by a method for tracking a particle filter tracker; Step S06: transmitting new conduit modeling information with the method for tracking the conduit, refreshing a display on an user interface, accurately coloring the conduit with the standard color, and changing a framed color as a standard conduit color and a background color accordingly.

Further, in Step S01, specifically, the 2D ultrasound image is scanned periodically with help of continuous rotation in space and the interior of the target environment is modeled using 3D modeling means.

Further, in Step S03, the framing of impurities outside the conduit is reduced provided that framing is performed.

Further, in Step S04, a specific method of obtaining the range for positioning the conduit is as follows: framed content is placed within a 3D frame, and the 3D frame is exactly sized to enclose only the framed content, to obtain the corresponding coordinate range within the 3D frame, that is, the range for positioning the conduit.

Further, a specific method for identifying the point cloud of the target conduit is as follows: Step S51, in an initialization step, downsampling the framed point cloud to reduce an amount of data; Step S52: extracting a Scale Invariant Feature Transform (SIFT) key point of the point cloud; Step S53: then calculating Signature of Histogram of Orientation (SHOT) features for the above key points, establishing a local coordinate system at the feature points, and combining spatial location information of neighboring points with geometric feature statistical information to describe the feature points; and Step S54: extracting the features, generating a feature vector, and inputting the feature vector into the support vector machine (SVM) classifier to obtain the point cloud of the target conduit.

Further, in Step S05, a point cloud obtained by an identifying module needs to be optimized, specifically: in Step S61: utilizing a direct-through filter, retaining a point cloud in an effective region, specifying ranges in x, y, and z latitudes, respectively, and filtering out the point cloud outside the range; and Step S62: downsampling the filtered point cloud to reduce the amount of data.

Preferably, the sampling method is geometric sampling.

Preferably, in Step S03, giving the content selected in the frame a red color, and in Step S06, the standard color is a blue color.

Beneficial Effects

The present invention is different from 3D magnetic field localization technology relied on by other 3D conduit navigation techniques, and is a method for identifying and tracking a 3D conduit based entirely on ultrasound localization, including the following steps: firstly rapidly modeling the conduit through an ultrasound map, then framing an approximate range of the conduit after human-computer interaction in a display interface, and tracking the approximate range accurately. The present invention has the following specific advantages of modeling and locating the conduit based on pure ultrasound; 2. faster and more accurate modeling; 3. more accurate positioning of the conduit by framing, reducing inaccurate positioning caused by other factors, and 4. human-machine interaction for positioning the conduit with ready access to ensure accuracy and reliability.

THE BEST EMBODIMENT OF THE PRESENT INVENTION

A method for identifying, localizing and tracking a calibrating conduit within a 3D ultrasound point cloud includes the following steps: Step S01: scanning periodically a 2D ultrasound image with help of continuous rotation in a space and modeling the interior of the target environment using 3D modeling means.

Step S02: performing human-computer interaction to locate and track a conduit in a user operation interface, and placing the conduit into a scannable range of an ultrasound probe.

Step S03: framing, by the human-computer interaction, the conduit, the after starting tracking and placing the conduit into the scannable range of the probe, changing a display interface accordingly, performing, by the user, human-computer interaction operation on a display interface to frame an area as small as possible to meet requirements where the conduit is located, that is, the framing of minimizing impurities outside the conduit provided that the conduit is framed; and giving the selected content in the frame a special color to distinguish therefrom; making, by the user, a determination whether the framing is correct, and if the framing is not correct, the user frames again until the effect meets the user's requirements and the conduit position is accurately identified.

DETAILED DESCRIPTION OF EMBODIMENTS

The present invention will be described in details below with reference to the drawings and embodiments.

Identification, locating and tracking of a common conduit lack a certain degree of reliability. When conducting experiments, a target environment introduced by the conduit and a fixed reference point can not be relatively removed. Otherwise, an accuracy rate is affected. Relying on ultrasound for conduit positioning and identification is a good solution to this problem, but there are some impurity interference in the ultrasound image. To more accurately locate and track the conduit, a method for identifying, localizing and tracking a calibrating conduit within a 3D ultrasound point cloud is proposed and includes the following steps: first acquiring an ultrasound image, then optimizing the ultrasound image, then generating the 3D point cloud, then optimizing the point cloud, then reconstructing the point cloud as a 3D model, adding an interface display, and then adding new conduit modeling information to the 3D model after the conduit is located and tracked.

Figure 1:
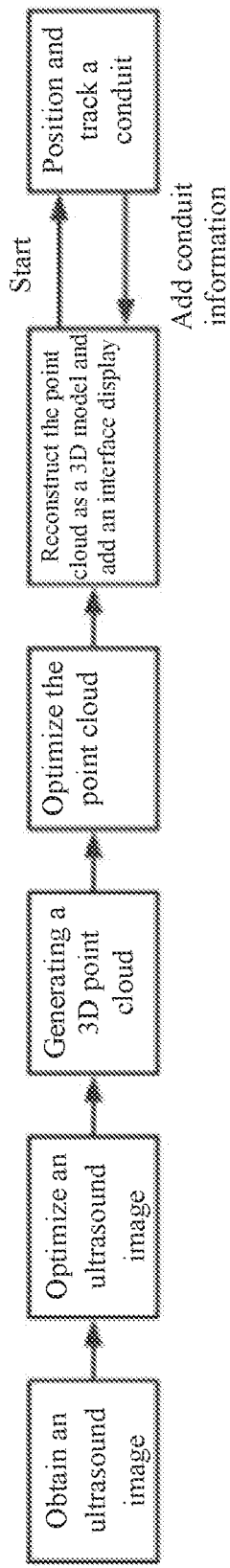
FIG. 1 is an overall flow chart of the present invention.

As shown in FIG. 1. Specific steps are as follows: Step S01: scanning periodically a 2D ultrasound image with help of continuous rotation in a space and modeling the interior of a target environment using 3D modeling means.

Step S02: performing human-computer interaction to locate and track a conduit in a user operation interface, and placing the conduit into a scannable range of an ultrasound probe.

Step S03: framing, by the human-computer interaction, the conduit, the after starting tracking and placing the conduit into the scannable range of the probe, changing a display interface accordingly, performing, by the user, human-computer interaction operation on a display interface to frame an area as small as possible to meet requirements where the conduit is located, that is, the framing of minimizing impurities outside the conduit provided that the conduit is framed; and giving the selected content in the frame a special color to distinguish therefrom; making, by the user, a determination whether the framing is correct, and if the framing is not correct, the user frames again until the effect meets the user's requirements and the conduit position is accurately identified.

In one embodiment, a special color is a red color.

After Step S04 meets the user's requirements and the location of the conduit is accurately identified, a minimum enclosing box algorithm (OBB) is performed on a selected target in a frame: the framed content is placed inside a stereo frame. The stereo frame is exactly sized to enclose only the framed content. At the same time, the corresponding coordinate range within the stereo frame is a range for localizing the conduit and transmitted to a conduit identification algorithm and a tracking algorithm, thus greatly reducing the possible noise interference, and causing ultrasound artifacts, etc. to affect the accuracy of modeling, and improving the accuracy of conduit identification.

Step S05: identifying and obtaining the point cloud of the target conduit, and taking the obtained point cloud as an input to obtain a field point cloud generated from a 2D ultrasound image by a method for tracking a particle filter tracker; the specific method of the identification to obtain the point cloud of the target conduit the specific method for identifying and obtaining the point cloud of the target conduit is as follows. Step S51, in an initialization step, downsampling the framed point cloud to reduce an amount of data; Step S52: extracting a SIFT key point of the point cloud; Step S53: then calculating SHOT features for the above key points, establishing a local coordinate system at the feature points, and combining spatial location information of neighboring points with geometric feature statistical information to describe the feature points; and Step S54: extracting the features, generating a feature vector, and inputting the feature vector into the SVM classifier to obtain the point cloud of the target conduit.

A particle filter tracker is initialized by using the point cloud obtained by the identifying module as an input. A scene point cloud generated from the 2D ultrasound image is obtained. The input scene point cloud is usually large in a data volume and there is a lot of invalid information, so the point cloud obtained by the identifying module needs to be optimized.

Firstly, a point cloud within a valid region is retained by using a direct-through filter. The point clouds outside the range are filtered out by specifying ranges in x, y and z latitudes, respectively. Secondly, the filtered point cloud is downsampled to reduce the amount of data.

In one embodiment, a sampling method is geometric sampling. The geometric sampling is characterized by sampling more points where the curvature of the point cloud is greater. The geometric sampling is computationally efficient, and the local point cloud is sampled uniformly, while stability is high, making the sampling results more noise resistant.

In one embodiment, the particle filter tracker herein is implemented based on a particle filtering algorithm. The advantage of the particle filtering algorithm for position estimation is that there is no linearization requirement for a system.

Figure 2:
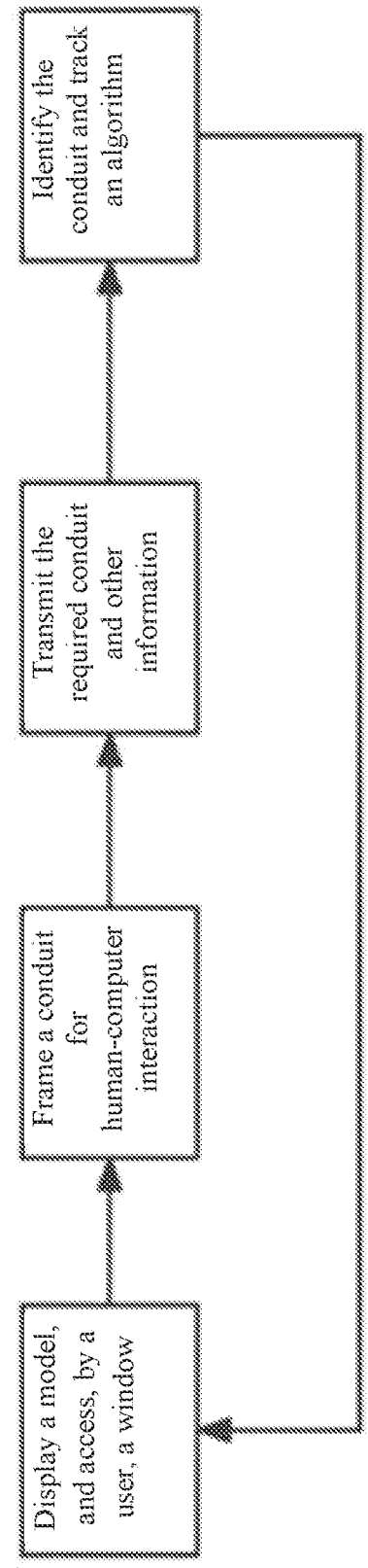
FIG. 2 is a flow chart of human-machine interaction guideline to identify and locate a conduit.

As shown in FIG. 2, after the above operation, a conduit tracking algorithm transmits new conduit modeling information and refreshes a display on interfaces of a model display and a user's use display window. The conduit is accurately colored as a standard color. The framed special color is changed to a standard conduit color and a background color accordingly. The above steps can also be repeated if additional requirements for conduit positioning are subsequently made.

In one embodiment, the standard color is a blue color.

INDUSTRIAL PRACTICABILITY

Further, this conduit localization algorithm reduces overall process time and provides a clearer and more real-time image of the conduit in a target environment compared with a conduit localization method such as electromagnetic localization, eliminating need for an overly demanding target environment and fixed reference points introduced by the conduit, while being more accurate than relying solely on ultrasound modeling.

The invention claimed is:

1. A method for identifying, localizing and tracking a calibrating conduit within a three-dimensional (3D) ultrasound point cloud, comprising the following steps:
    Step S01: modeling an interior of a target environment;
    Step S02: performing human-computer interaction to locate a conduit in a user operation interface, and placing the conduit into a scannable range of an ultrasound probe;
    Step S03: after starting tracking and placing the conduit into the scannable range of the probe, performing, by the user, human-computer interaction operation on a display interface to frame an area where the conduit is located, and giving content in the frame a color to distinguish therefrom; making, by the user, a determination whether a conduit position is accurate, and if the framing is not correct, the user frames again until the conduit position is accurately identified;
    Step S04: after the conduit position is accurately identified, obtaining a range for positioning the conduit, and identifying and tracking the conduit;
    Step S05: identifying and obtaining a point cloud of the target conduit, and taking the obtained point cloud as an input to obtain a field point cloud generated from a two-dimensional (2D) ultrasound image by a method for tracking a particle filter tracker; and
    Step S06: transmitting new conduit modeling information with the method for tracking the conduit, refreshing a display on a user interface, accurately coloring the conduit with a standard color, and changing a framed color as a standard conduit color and a background color accordingly;
    wherein in Step S04, a specific method of obtaining the range for positioning the conduit is as follows: framed content is placed within a 3D frame, and the 3D frame is exactly sized to enclose only the framed content, to obtain a corresponding coordinate range within the 3D frame, which is a range for positioning the conduit.

2. The method according to claim 1, wherein in Step S03, giving the content selected in the frame a red color, and in Step S06, the standard color is a blue color.

3. The method according to claim 1, wherein in Step S01, the 2D ultrasound image is scanned periodically with help of continuous rotation in space, and the interior of the target environment is modeled using 3D modeling means.

4. The method according to claim 3, wherein in Step S05, a specific method for identifying the point cloud of the conduit is as follows:
    Step S51, in an initialization step, downsampling a framed point cloud to reduce an amount of data;
    Step S52: extracting a Scale Invariant Feature Transform (SIFT) key point of the point cloud;
    Step S53: then calculating Signature of Histogram of Orientation (SHOT) features for the SIFT key points, establishing a local coordinate system at the feature points, and combining spatial location information of neighboring points with geometric feature statistical information to describe the feature points; and
    Step S54: extracting the features, generating a feature vector, and inputting the feature vector into a support vector machine (SVM) classifier to obtain the point cloud of the conduit.

5. The method according to claim 3, wherein in Step S03, giving the content selected in the frame a red color, and in Step S06, the standard color is a blue color.

6. The method according to claim 1, wherein in Step S03, a framing of impurities outside the conduit is reduced provided that framing is performed.

7. The method according to claim 6, wherein in Step S05, a specific method for identifying the point cloud of the conduit is as follows:
    Step S51, in an initialization step, downsampling a framed point cloud to reduce an amount of data;
    Step S52: extracting a Scale Invariant Feature Transform (SIFT) key point of the point cloud;
    Step S53: then calculating Signature of Histogram of Orientation (SHOT) features for the SIFT key points, establishing a local coordinate system at the feature points, and combining spatial location information of neighboring points with geometric feature statistical information to describe the feature points; and Step S54: extracting the features, generating a feature vector, and inputting the feature vector into a support vector machine (SVM) classifier to obtain the point cloud of the conduit.

8. The method according to claim 6, wherein in Step S03, giving the content selected in the frame a red color, and in Step S06, the standard color is a blue color.

9. A method for identifying, localizing and tracking a calibrating conduit within a three-dimensional (3D) ultrasound point cloud, comprising the following steps:
   Step S01: modeling an interior of a target environment;
   Step S02: performing human-computer interaction to locate a conduit in a user operation interface, and placing the conduit into a scannable range of an ultrasound probe;
   Step S03: after starting tracking and placing the conduit into the scannable range of the probe, performing, by the user, human-computer interaction operation on a display interface to frame an area where the conduit is located, and giving content in the frame a color to distinguish therefrom; making, by the user, a determination whether a conduit position is accurate, and if the framing is not correct, the user frames again until the conduit position is accurately identified;
   Step S04: after the conduit position is accurately identified, obtaining a range for positioning the conduit, and identifying and tracking the conduit;
   Step S05: identifying and obtaining a point cloud of the conduit, and taking the obtained point cloud as an input to obtain a field point cloud generated from a two-dimensional (2D) ultrasound image by a method for tracking a particle filter tracker; and
   Step S06: transmitting new conduit modeling information with the method for tracking the conduit, refreshing a display on a user interface, accurately coloring the conduit with a standard color, and changing a framed color as a standard conduit color and a background color accordingly;
   wherein in Step S05, a specific method for identifying the point cloud of the conduit is as follows:
   Step S51, in an initialization step, downsampling a framed point cloud to reduce an amount of data;
   Step S52: extracting a Scale Invariant Feature Transform (SIFT) key point of the point cloud;
   Step S53: then calculating Signature of Histogram of Orientation (SHOT) features for the SIFT key points, establishing a local coordinate system at the feature points, and combining spatial location information of neighboring points with geometric feature statistical information to describe the feature points; and
   Step S54: extracting the features, generating a feature vector, and inputting the feature vector into a support vector machine (SVM) classifier to obtain the point cloud of the conduit.

10. The method according to claim 9, wherein in Step S05, a point cloud obtained by an identifying module needs to be pre-processed by:
   Step S61: utilizing a direct-through filter, retaining the point cloud in an effective region, specifying ranges in x, y, and z latitudes, respectively, and filtering out the point cloud outside the range; and
   Step S62: downsampling the filtered point cloud to reduce the amount of data.

11. The method according to claim 10, wherein in Step S03, giving the content selected in the frame a red color, and in Step S06, the standard color is a blue color.

12. The method according to claim 10, wherein in Step S62, a sampling method is geometric sampling.

13. The method according to claim 12, wherein in Step S03, giving the content selected in the frame a red color, and in Step S06, the standard color is a blue color.

* * * * *